(12) United States Patent
Moser et al.

(10) Patent No.: US 6,168,632 B1
(45) Date of Patent: Jan. 2, 2001

(54) FEMUR COMPONENT OF A HIP JOINT ENDOPROSTHESIS

(75) Inventors: Walter Moser, Kaufdorf; Anton Cotting, Grenchen, both of (CH)

(73) Assignee: Mathys Medizinaltechnik AG, Bettlach (CH)

( * ) Notice: Under 35 U.S.C. 154(b), the term of this patent shall be extended for 0 days.

(21) Appl. No.: 09/308,970
(22) PCT Filed: Nov. 29, 1996
(86) PCT No.: PCT/CH96/00421
 § 371 Date: May 27, 1998
 § 102(e) Date: May 27, 1999
(87) PCT Pub. No.: WO98/23231
 PCT Pub. Date: Jun. 4, 1998
(51) Int. Cl.$^7$ ...................................... A61F 2/32
(52) U.S. Cl. ........................................ 623/23.31
(58) Field of Search ........................ 623/22, 23

(56) References Cited

FOREIGN PATENT DOCUMENTS

| 35 05 997 | 11/1985 | (DE) . | |
| 3505997 | * 11/1985 | (DE) | ...................................... 623/23 |
| 0135755 | * 4/1985 | (EP) | ...................................... 623/23 |
| 222 236 | 5/1987 | (EP) . | |
| 378 044 | 7/1990 | (EP) . | |
| 669 116 | 8/1995 | (EP) . | |
| 2699398 | * 6/1994 | (FR) | ...................................... 623/23 |

* cited by examiner

Primary Examiner—David J. Isabella
(74) Attorney, Agent, or Firm—Pearne & Gordon LLP

(57) ABSTRACT

A femur component of a hip joint endoprosthesis which has a shaft (1) for anchoring in the medullary cavity of the femur. The shaft (1) has a distal section (9) and a proximal section (8), to which is connected a collar section (2) with a peg (3) for receiving an articular head, or with an articular head which is firmly attached to the collar section (2). The shaft (1) has a front surface (4), a rear surface (5), a lateral side (6), a mesial side (7) and a plane of symmetry (11), whereby longitudinal ribs (10) which stretch from proximal to distal are fitted on the front surface (4) and the rear surface (5) in the proximal section (8) of the shaft (1). The crests (12) of the longitudinal ribs (10) form an angle δ/2 of at least 1° to the plane of symmetry (11), and the envelope of the crests (123) of the longitudinal ribs (10) forms a double wedge-like or ellipsoid body, which tapers both toward the lateral side (6) and the mesial side (7).

25 Claims, 1 Drawing Sheet

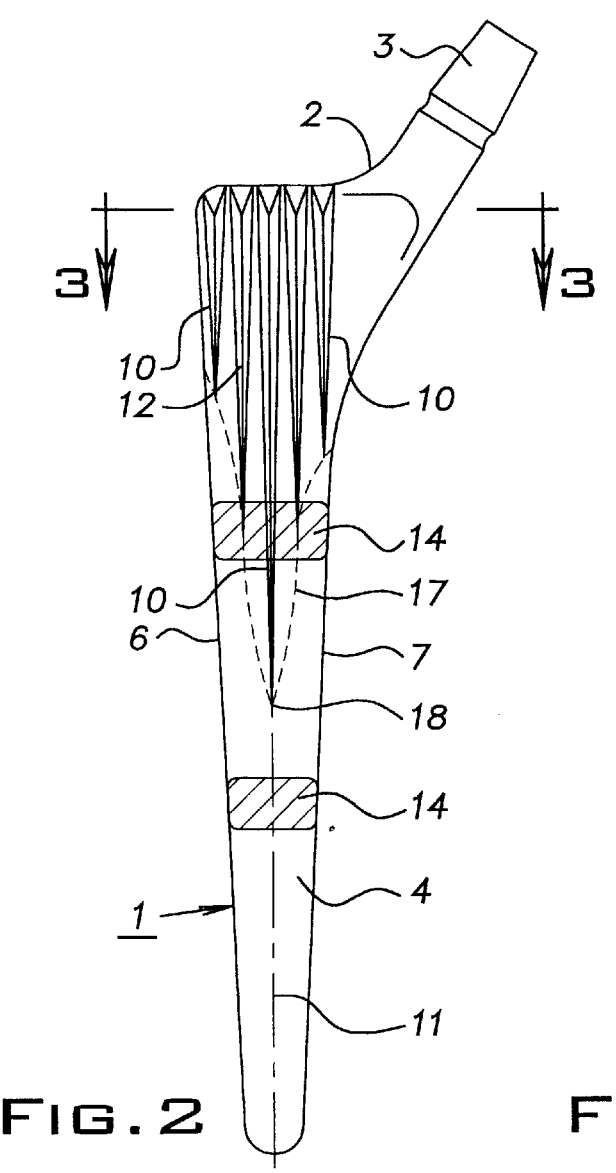
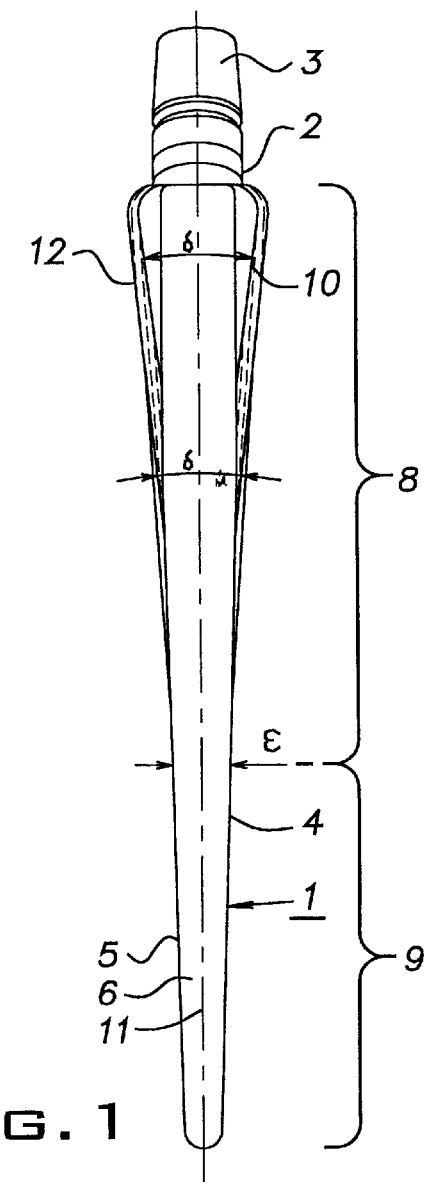
FIG. 2          FIG. 1
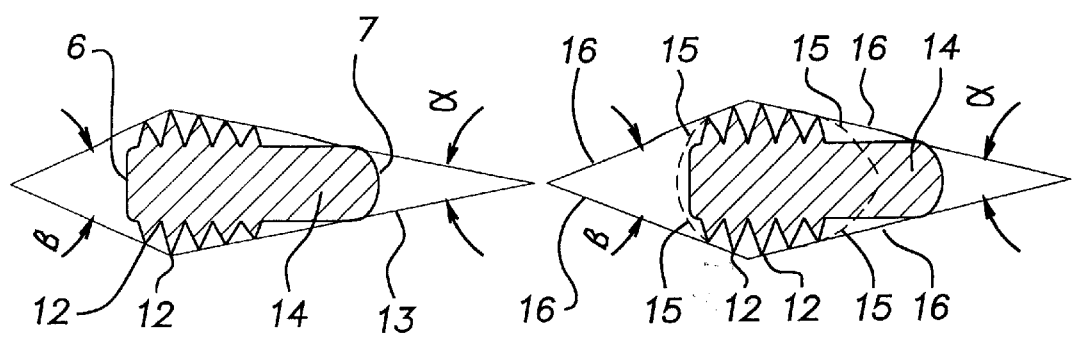
FIG. 3          FIG. 4

FEMUR COMPONENT OF A HIP JOINT ENDOPROSTHESIS

FIELD OF THE INVENTION

This invention relates to a femur component of a hip-joint endoprosthesis with a shaft to be anchored in the femur's marrow cavity having a distal segment and a proximal segment joined by a neck with a stub to receive a hinge head or with a hinge head firmly adjoining the neck and also including a posterior surface, a lateral side, a mesial side and a plane of symmetry, longitudinal ribs extending in the proximal-to-distal direction on the anterior surface and on the posterior surface in the proximal segment of the shaft.

BACKGROUND OF THE INVENTION

Femur components of this general type are known from the state of the art, but they incur various drawbacks.

As regards un-cemented femur prostheses for hip-joint replacement, the primary stabilization of the femur shaft is implemented by frictionally and geometrically locking onto the enclosing bone. The femur shaft is configured in such a way that loading it entails its being wedged into the bony support. In particular, during the first loading phase wherein some seating shifts of the femur shaft are likely, a suitable configuration must assure reliable primary affixation. In the event of a seating shift, new stabilization must be assured by suitable reconfiguration. In the absence of adequate primary stability, loading will entail repeated shifts at the boundary surface between femur shaft and bone, preventing reliable implant bodily incorporation. On the other hand, if the primary anchoring is reliable, the implant can be enclosed by the bone tissue during the healing process and offer good long-term prospects.

Preferably, the primary affixation is in the upper portion of the prosthesis shaft enclosed by the spongy bone. A large support surface can be achieved in the big bone volume present therein. Seen biomechanically and clinically, it has been advantageous to apply the force through this region.

Illustratively, a femur shaft is on the market wherein the proximal shaft portion intended to be anchored in the spongy bone structure continuously tapers conically in the lateral-to-mesial direction in order to secure renewed, automatic clamping in the event the bone yields in the mesial direction. The region of the trochanter major with the anchoring space, however, does not have a cross-sectionally triangular or trapezoidal shape, but rather an oval one. Accordingly, this known femur shaft suffers from the drawback that the laterally much enlarged proximal shaft portion may crack the bone. In addition, this known femur shaft comprises solid ribs which when displacing bone volume raises the pressure and may further contribute to the cracking effect.

A longitudinal section of the proximal femur with an inserted femur shaft shows that the spongy substance is not sharply delimited to the trochanter region but instead partly continues as far as the zone of the diaphyseal bone tube. However, as much as possible of this bone structure should be used to transmit the load. But the ribs located in one position of the known femur shaft do not optimally meet this requirement because of the little differentiated configuration. The point of contact and the elongation of the ribs at the shaft should be designed in such manner that as much as possible of the spongy volume of the proximal femur is used for anchoring.

SUMMARY OF THE INVENTION

An object of the invention is to provide a femur component of a hip-joint endoprosthesis optimally corresponding to the spongy architecture in the proximal femur part and entailing cementless, primary shaft anchoring in the femur in the most stable possible manner to secure thereby good likelihood of bone healing.

The double-wedge or ellipsoidal shape of the proximal shaft segment offers the advantage that the prostheses shaft can wedge itself both laterally and mesially in the event of a seating shift. The oval envelope curve of the ribs matching the cross-section of the proximal femur minimizes the danger of cracking the proximal femur due to direct pressure on the hard cortical bone.

In a preferred further development of the invention, wherein the ribs are cross-sectionally triangular, these ribs easily penetrate the spongy bone volume and, as a result, the pressure is reduced during the insertion procedure. Because, preferably, the triangular ribs extend conically, additional wedging is achieved that is lacking in rectangular ribs such as are used in the state of the art.

The straightness of the shaft together with the increasing height in the proximal direction of the ribs extending in the direction of the shaft axis allows secure positioning of the femur shaft and knocking it into place with guidance by the self-cutting ribs. If, on the other hand, the ribs are partly or all mounted at an angle to the shaft axis, no seat enclosing the ribs can be realized when installing the femur shaft. Because the rib projection varies along the shaft, the stress on the spongy volume is more homogeneous than in known shafts with ribs beginning at a given height which then continuously increases.

Another preferred development consists in that the combs of the longitudinal ribs subtend an angle ½δ of at least 1°, preferably at least 2° with the plane of symmetry. The individual combs of the longitudinal ribs subtend different angles ½δ in the range of 3 to 8° with the plane of symmetry, preferably the longitudinal ribs situated closer to the lateral and the mesial side subtending a larger angle ½δ than those in between. Such a rib geometry functionally stimulates the enclosing bone, whereas such a stimulus is not achieved with the dull rib shape of the state of the art. This functional stimulus causes bone regeneration in the stressed zone with ensuing compaction and hence bone healing. The blood supply to the regenerated bone can optimally form in the troughs of this rib structure.

Appropriately, the anterior and posterior surfaces form a wedge tapering toward the distal segment, the central plane being the plane of symmetry, the angle ε of the wedge being in the range of 0.5 to 3.0°, preferably within 1.0 and 2.0°. On account of this geometry, the wedging effect is continued also along the upper shaft zone. In case subsequent intervention is due on a solidly integrated shaft, the shaft is more easily knocked free if its geometry is conical in all directions, that is, also proximally in the intra-rib zone, than if the geometry were other than conical.

Seen in a section orthogonal to the plane of symmetry, the envelope curve of the combs of the longitudinal ribs is approximately in the form of a kite quadrilateral of which the sides may approximately represent straight lines or arcs of circular or elliptical segments.

Relative to the mesial side, the kite quadrilateral should subtend an inside angle α larger than 10°, and preferably larger than 12°. In addition, the inside angle α should be less than 22°, preferably less than 20°.

Toward the lateral side, the kite quadrilateral should subtend an inside angle β larger than 8°, preferably larger than 9°. Moreover the inside angle β should be less than 45°, preferably less than 40°.

Appropriately, the longitudinal-rib combs are sharp and, seen in a section orthogonal to the plane of symmetry, are preferably triangular. Illustratively, the longitudinal ribs may assume the shape of three-sided pyramids of which the vertices point distally. The longitudinal-rib combs, however, may also be rounded and, seen in a section orthogonal to the plane of symmetry, preferably are semi-circular. On the other hand, uniformly thick longitudinal ribs of rectangular cross-section are to be avoided.

Preferably in a continuous manner, the width of the longitudinal ribs appropriately decreases from the proximal to the distal sides. This also applies to the height of the longitudinal ribs which preferably continuously decrease in the proximal-to-distal direction.

Surprisingly especially good clinical results were observed when at least one of the longitudinal ribs runs as far as the distal half of the shaft because this makes possible increased primary stability and because bone regeneration or bone transformation propagates proximally from this anchoring zone in the form of osteo-conduction.

Further advantages may be achieved using embodiments wherein the shaft is without a collar and assumes a substantially rectangular cross-section as seen in a section orthogonal to the plane of symmetry.

BRIEF DESCRIPTION OF THE DRAWINGS

The invention and its further developments are elucidated below with reference to several embodiments shown in the partly schematic figures wherein:

FIG. 1 is an elevation of the femur component of the invention seen from the anterior side and with two cross-sectional contours, FIG. 2 is an elevation of the femur component of FIG. 2 seen from the lateral side, FIG. 3 is a section of the femur component of FIG. 1 along line III—III and FIG. 4 is a section similar to that of FIG. 3 with a modified envelope curve of the longitudinal-rib combs.

DETAILED DESCRIPTION OF PREFERRED EMBODIMENTS

The femur component of a hip-joint endoprosthesis shown in FIGS. 1 through 3 essentially comprises a shaft 1 without a collar and with a distal segment 9 and a proximal segment 8 adjoined by a neck 2 with a stub 3 to receive a conventional pivot head, or by a pivot head firmly joined to neck 2. Shaft 1 comprises an anterior surface 4, a posterior surface 5, a lateral side 6, a mesial side 7 and a plane of symmetry 11 identical with the plane of FIG. 1. Shown in a section orthogonal to the plane of symmetry 11, the shaft is of a substantially rectangular cross-section 14.

Longitudinal ribs 10 are on anterior and posterior surfaces 4 and 5, respectively, in the proximal segment 8 of shaft 1 and extend from the proximal side to the distal side. Depending on their positions, combs 12 of longitudinal ribs 10 subtend and an angle ½δ of 3° to 8° with plane of symmetry 11. Longitudinal ribs 10 near lateral side 6 and mesial side 7 subtend a larger angle ½δ than longitudinal ribs 10 in between. Moreover, individual longitudinal ribs 10 are of different lengths, preferably those located toward lateral side 6 and mesial side 7 being shorter than those in between. The line 17 connecting ends 18 of the longitudinal ribs 10 merging into anterior and posterior surfaces 4, 5 do not lie on a straight line but, instead, lie on a parabolic or ellipsoidal curve.

The envelope curves of combs 12 of longitudinal ribs 10 subtend a double wedge or an ellipsoidal body tapering both in the direction of lateral side 6 and in the direction of mesial sides 6, 7.

Furthermore, anterior surface 4 together with posterior surface 5 forms a wedge 4, 5 tapering toward distal segment 9, the plane of symmetry 11 being the center plane, and the wedge angle ε of wedge 4, 5 being 0.5°.

As shown in FIG. 3, when seen in a section orthogonal to the plane of symmetry 11, the envelope curve of combs 12 of longitudinal ribs 10 form a kite quadrilateral 13, the quadrilateral's short sides pointing laterally and its long sides pointing mesially.

The inside angle α of kite quadrilateral 13 is 12° to 20° toward the mesial side 7 and its inside angle β toward lateral side 6 is from 9° to 44°.

Combs 12 of longitudinal ribs 10 are sharp and, when seen in a section orthogonal to the plane of symmetry 11, each of their contours is triangular. The width and height of longitudinal ribs 10 decrease continuously in the proximal-to-distal direction. Accordingly, longitudinal ribs 12 form three-sided pyramids, the vertex of the pyramid pointing distally. Therefore, the troughs between individual longitudinal ribs 10 narrow from distal segment 9 to proximal segment 8.

As shown in FIG. 1, one of longitudinal ribs 12, namely the center one, extends as far as the distal half of shaft 1 and thereby enhances the primary stability of the implanted shaft.

The envelope curve of combs 12 of the longitudinal ribs 10, shown as a kite quadrilateral 13 in FIG. 3, also may comprise slightly outward bulging, for instance arcuate, envelope curves 15, as shown in FIG. 4. In this embodiment angles α and β relate to the inside angles of the kite quadrilateral formed by tangents 16 to the convex envelope curves.

What is claimed is:

1. A femur component for a hip joint endoprosthesis comprising:
   a shaft (1) to be anchored in a marrow cavity of a femur, said shaft having a distal segment (9) and a proximal segment (8), said shaft further comprising an anterior surface (4), a posterior surface (5), a lateral side (6), a mesial side (7) and a plane of symmetry (11);
   a neck (2) attached to said proximal segment (8), said neck being adapted to receive a pivot head; and
   a plurality of longitudinal ribs (10) extending in the proximal to distal direction on said anterior surface (4) and on said posterior surface (5) on said proximal segment (8) of said shaft (1), outwardly facing edges of said ribs comprising a comb structure, said edges lying in a double wedge or ellipsoidal surface tapering in the direction of both said lateral side (6) and said mesial side, wherein a width of each longitudinal rib decreases continuously in the proximal to distal direction, and a height of each longitudinal rib decreases continuously in the proximal to distal direction.

2. A femur component according to claim 1 wherein said edges of said comb subtend an angle ½δ of at least 1° with said plane of symmetry (11).

3. A femur component according to claim 2 wherein said edges of said comb subtend an angle ½δ of at least 2° with said plane of symmetry (11).

4. A femur component according to claim 2 wherein said edges of said comb subtend an angle ½δ in the range of 3° to 8° with said plane of symmetry (11), said longitudinal ribs

(10) situated nearest said lateral side (6) and said mesial side (7) subtending a larger angle than said ribs in between.

5. A femur component according to claim 1 wherein said anterior surface (4) and said posterior surface (5) form a wedge tapering toward said distal segment (9) with said place of symmetry (11) forming a center plane of said wedge, said surfaces of said wedge subtending an angle e in the range of 0.5° to 3.0°.

6. A femur component according to claim 5 wherein said angle ϵ is in the range of 1.0° to 2.0°.

7. A femur component according to claim 1 wherein said longitudinal ribs differ from each other in length with ribs nearest said lateral side (6) and said mesial side (7) being shorter than ribs intermediately located.

8. A femur component according to claim 1 wherein said edges of said comb structure are sharp and wherein said ribs, as seen in a section orthogonal to said plane of symmetry, are triangular.

9. A femur component according to claim 1 wherein said edges of said comb structure are rounded and wherein said ribs, as seen in a section orthogonal to said plane of symmetry, are semi-circular.

10. A femur component according to claim 1 wherein at least one of said longitudinal ribs extends distally to a lengthwise midpoint of said shaft.

11. A femur component according to claim 1 wherein said outwardly facing edges of a plurality of said longitudinal ribs on said anterior and posterior sides lie in planes intersecting near said mesial side (7) to form an inside angle larger than 10°.

12. A femur component according to claim 1 wherein said outwardly facing edges of a plurality of said longitudinal ribs on said anterior and posterior sides lie in planes intersecting near said mesial side (7) to form an inside angle larger than 12°.

13. A femur component according to claim 12 wherein said inside angle is less than 22°.

14. A femur component according to claim 12 wherein said inside angle is less than 20°.

15. A femur component according to claim 1 wherein said outwardly facing edges of a plurality of said longitudinal ribs on said anterior and posterior sides lie in planes intersecting near said lateral side (7) to form an inside angle larger than 8°.

16. A femur component according to claim 15 wherein said inside angle is larger than 9°.

17. A femur component according to claim 15 wherein said inside angle is smaller than 45°.

18. A femur component according to claim 15 wherein said inside angle is smaller than 40°.

19. A femur component according to claim 1 wherein said shaft has no collar.

20. A femur component according to claim 1 wherein said shaft (1) is substantially rectangular in section orthogonal to said plane of symmetry.

21. A femur component according to claim 1 wherein said longitudinal ribs are in the form of three-sided pyramids with vertices pointing distally.

22. A femur component according to claim 1 wherein said outwardly facing edges of a plurality of said longitudinal ribs on said anterior and posterior sides lie in an envelope curve comprising a kite quadrilateral.

23. A femur component according to claim 1 wherein said outwardly facing edges of a plurality of said longitudinal ribs on said anterior and posterior sides lie in an envelope curve comprising an ellipsoid or a lenticular shape.

24. A femur component according to claim 1 wherein distal extremities of said longitudinal ribs on said anterior and posterior surfaces lie on a curve which is parabolic or elliptic.

25. A femur component according to claim 1 wherein troughs between said longitudinal ribs decrease in width from said distal segment toward said proximal segment.

* * * * *